US009414999B2

(12) United States Patent  
Paul et al.

(10) Patent No.: US 9,414,999 B2
(45) Date of Patent: Aug. 16, 2016

(54) METHOD OF TREATING HAIR

(71) Applicant: Conopco, Inc., Englewood Cliffs, NJ (US)

(72) Inventors: Prem Kumar Cheyalazhagan Paul, Spital (GB); Susan Pye, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 14/401,000

(22) PCT Filed: May 15, 2013

(86) PCT No.: PCT/EP2013/060102
§ 371 (c)(1),
(2) Date: Nov. 13, 2014

(87) PCT Pub. No.: WO2013/174703
PCT Pub. Date: Nov. 28, 2013

(65) Prior Publication Data
US 2015/0128984 A1     May 14, 2015

(30) Foreign Application Priority Data
May 21, 2012   (EP) .................................... 12168630

(51) Int. Cl.
A61Q 5/04       (2006.01)
A61K 8/60       (2006.01)
A61K 8/365      (2006.01)
A61K 8/49       (2006.01)
A45D 7/06       (2006.01)
A61K 8/34       (2006.01)
A61K 8/362      (2006.01)

(52) U.S. Cl.
CPC ... A61K 8/60 (2013.01); A45D 7/06 (2013.01); A61K 8/345 (2013.01); A61K 8/362 (2013.01); A61K 8/365 (2013.01); A61K 8/498 (2013.01); A61Q 5/04 (2013.01)

(58) Field of Classification Search
None
See application file for complete search history.

(56) References Cited

U.S. PATENT DOCUMENTS 3,025,218 A     3/1962   Strain
4,349,537 A     9/1982   Forbriger, Jr.
4,409,204 A    10/1983   Lang

FOREIGN PATENT DOCUMENTS

| EP | 1393708 | 3/2004 |
| WO | WO03039497 A1 | 5/2003 |
| WO | WO2005025524 A1 | 3/2005 |
| WO | WO2005084622 | 9/2005 |
| WO | WO2005084623 | 9/2005 |
| WO | WO2009047251 | 4/2009 |
| WO | WO2009138288 A1 | 11/2009 |
| WO | WO2010049434 A2 | 5/2010 |
| WO | WO2010141098 | 12/2010 |
| WO | WO2012084532 | 6/2012 |
| WO | WO2013174575 A1 | 11/2013 |

OTHER PUBLICATIONS

IPRP2 in PCTEP2013060102—Corrected Version dated May 16, 2014; p. 1 to p. 11.
IPRP2 in PCTEP2013060102 dated May 15, 2014; p. 12 to p. 22.
Search Report EP13157663 dated Aug. 28, 2013; p. 23 to p. 24.
Search Report in EP12168630 dated Oct. 12, 2012; p. 25 to p. 26.
Search Report in EP12168631 dated Oct. 11, 2012; p. 27 to p. 28.
Search Report in PCTEP2013057809 dated Jul. 17, 2013; p. 29 to p. 32.
Search Report in PCTEP2013060102 dated Jul. 17, 2013; p. 33 to p. 35.
Written Opinion in EP12168630 dated Oct. 12, 2012; p. 36 to p. 38.
Written Opinion EP13157663 dated Aug. 28, 2013; p. 39 to p. 39.
Written Opinion in EP12168631 dated Oct. 11, 2012; p. 40 to p. 42.
Written Opinion in PCTEP2013057809 dated Jul. 17, 2013; p. 43 to p. 49.
Written Opinion in PCTEP2013060102 dated Jul. 17, 2013; p. 50 to p. 54.

*Primary Examiner* — Jyothsna Venkat
(74) *Attorney, Agent, or Firm* — Greenberg Traurig, LLP

(57) ABSTRACT

A method of straightening the hair comprising the step of applying to the hair a hair treatment composition comprising: i) at least 0.4 wt % of the total composition of a sugar alcohol; and ii) at least 0.4 wt % of the total composition of a bi or tridentate carboxylic acid in which the ratio of sugar alcohol to acid is 1:5 to 5:1; and iii) heating the resulting composition to a temperature of greater than 120° C. for at least 10 seconds.

7 Claims, No Drawings

METHOD OF TREATING HAIR

The invention relates to a method of hair straightening.

The current hair market has a wide range of straightening products. A common way to retain a particular hairstyle is by applying a hairspray, mousses, gel, lotions or wax. The materials in these compositions are generally film forming agents, resins, gums, and/or adhesive polymers. Generally these formulations do not straighten the hair from wash to wash.

Permanent hair straightening compositions that are on the market are based on chemical treatment of the hair in a two-step process using thiol- or hydroxide-based reducing agents followed by a neutralisation or oxidation step. Such systems have various negatives associated with them; in that the process itself is difficult to conduct, in many instances this straightening process is undertaken by a qualified hairdresser in a professional salon. Furthermore the straightening process damages the hair, has an unpleasant odor and can cause irritation to the scalp.

WO2007/047251 discloses styling/straightening compositions containing isomalt;

The present invention has now found that hair can be straightened in a way that mitigates damage, yet remains straight/has reduced volume even after subsequent washing.

SUMMARY OF INVENTION

The present invention relates to a method of straightening the hair comprising the step of applying to the hair a hair treatment composition comprising:
i) at least 0.4 wt % of the total composition of a sugar alcohol; and
ii) at least 0.4 wt % of the total composition of a bi or tridentate carboxylic acid in which the ratio of sugar alcohol to acid is 1:5 to 5:1; and
iii) heating the resulting composition to a temperature of greater than 120° C. for at least 10 seconds.

DESCRIPTION OF INVENTION

The composition of the invention comprise a sugar alcohol, preferably the sugar alcohol comprises mannitol and/or sorbitol, more preferably the sugar alcohol is a mono or disaccharide disaccharide. Particularly preferred are isomalt and/or sorbitol. Isomalt is a combination of 1-O-•-D-glucopyranosido-D-mannitol and 6-O-•-D-glucopyranosido-D-sorbitol.

The level of sugar alcohol in the total composition is preferably from 0.4 to 7.9 wt % preferably, more preferably from 1 wt % to 7 wt % of the total composition, most preferably from 1.5 to 6 wt %.

Compositions of the invention comprise a bidentate or tridentate organic acids. Preferably the organic acid is a di or tri carboxylic acid, more preferably the carboxylic cid is a short chain (C2-C10, preferably C3 to C6)) carboxylic acids, especially preferred are di or tri acid carboxylic acid, citric acid being particularly preferred.

The bi or tridentate carboxylic acid is present in the total composition at a level of at least 0.4 wt %, more preferably at al level greater than 0.9 wt %, most preferably at a level from 1 to 5 wt %.

The ratio of sugar alcohol to bi.tridentate carboxylic acid is from 1:5 to 5:1, more preferably from 1:3 to 3:1.

Hair care compositions of the present invention can comprise a carrier, or a mixture of such carriers, which are suitable for application to the hair. The carriers are present at from about 0.5% to about 99.5%, preferably from about 5.0% to about 99.5%, more preferably from about 10.0% to about 98.0%, of the composition. As used herein, the phrase "suitable for application to hair" means that the carrier does not damage or negatively affect the aesthetics of hair or cause irritation to the underlying skin.

Compositions according to the invention comprise a buffer or pH adjuster. Preferred buffers or pH adjusters include weak acids and bases such glycine/sodium hydroxide, lactic acid, succinic acid, acetic salt and salts thereof. Frequently a mixture of buffering system. Preferably the pH is 4 or below. More preferably the pH is from 2.5 to 3.5.

Compositions according to the invention are preferably aqueous compositions intended to be applied to the hair after shampooing and rinsing. They are massaged into preferably dry hair and, heating, preferably followed by further rinsing with water prior to drying the hair. By aqueous composition, it is meant that the compositions of the invention comprise 60% by weight or more of water, preferably 70% or more, more preferably 80% or more.

When the hair care composition is a hair spray, tonic, gel, or mousse the preferred solvents include water, ethanol, volatile silicone derivatives, and mixtures thereof. The solvents used in such mixtures may be miscible or immiscible with each other. Mousses and aerosol hair sprays can also utilise any of the conventional propellants to deliver the material as a foam (in the case of a mousse) or as a fine, uniform spray (in the case of an aerosol hair spray). Examples of suitable propellants include materials such as trichlorofluoromethane, dichlorodifluoromethane, difluoroethane, dimethylether, propane, n-butane or isobutane. A tonic or hair spray product having a low viscosity may also utilise an emulsifying agent. Examples of suitable emulsifying agents include nonionic, cationic, anionic surfactants, or mixtures thereof. If such an emulsifying agent is used, it is preferably present at a level of from about 0.01% to about 7.5% by weight based on total weight of the composition. The level of propellant can be adjusted as desired but is generally from about 3% to about 30% by weight based on total weight for mousse compositions and from about 15% to about 50% by weight based on total weight for aerosol hair spray compositions.

Hair styling creams or gels also typically contain a structurant or thickener, typically in an amount of from 0.01% to 10% by weight.

Suitable spray containers are well known in the art and include conventional, non-aerosol pump sprays i.e., "atomisers", aerosol containers or cans having propellant, as described above, and also pump aerosol containers utilising compressed air as the propellant.

The formulation may include conditioning materials such as surfactants, cationic conditioners suitable for hair, quaternary silicone polymers, silicone based conditioners and their emulsions, and amino functional silicones and their emulsions.

Further general ingredients suitable for all product forms include, sun-screening agents, anti-dandruff actives, carboxylic acid polymer thickeners and emulsifiers for emulsifying the various carrier components of the compositions of the invention.

In some aspects of this invention it is highly desirable if the composition comprises a styling aid. Particularly useful as styling aids with this invention are hair styling polymers. Hair styling polymers are well known articles of commerce and many such polymers are available commercially which contain moieties which render the polymers cationic, anionic, amphoteric or nonionic in nature. The polymers may be synthetic or naturally derived.

The amount of the hair styling polymer may range from 0.1 to 10%, preferably 0.5 to 8%, more preferably 0.75 to 6% by weight based on total weight of the composition.

The compositions of the present invention may also contain adjuncts suitable for hair care. Generally such ingredients are included individually at a level of up to 2, preferably up to 1 wt % of the total composition. Suitable hair care adjuncts, include amino acids, sugars and ceramides.

The method of the invention comprises applying compositions of the invention followed by a heating step. The hair should be heated to a temperature above 120° C., more preferably above 150° C., most preferably above 170° C. It is preferable if the maximum temperature applied to the hair is 220° C.

The following non-limiting Examples further illustrate the preferred embodiments of the invention. All percentages referred to in the examples and throughout this specification are by weight based on total weight unless otherwise indicated.

EXAMPLES

Dark brown European wavy #6 switches of length ~25 cm and weight 2 gms, were dosed with 1 ml each of 4% citric acid (4% C); 4% sorbitol (4% S), 2% citric acid+2% sorbitol (2% C+2% S), 4% isomalt (4% I), 2% citric acid+2% isomalt (2% C+2% I) solutions. Control switches were treated with water. They were left to dry at 50° C. for at least 30 minutes. When dry the switches were straightened 7 times with irons (set at 180° C.). The switches were washed with Sunsilk (Fresh & Flowing) twice for 30 secs each time. They were left to dry overnight at 20° C. & 50% RH. The switches were combed 5 times and pictures taken. The volume and length of switches are measures of the straightness of the treated switches. (Here volume refers to the projection of the switch image on to the screen and is given in mm$^2$).

| Treatment | Volume in mm$^2$ | % Volume reduction compared to water | Length in mm | % Length benefit compared to water2 |
|---|---|---|---|---|
| water | 13932 | 0.0 | 199.5 | 0.0 |
| 4% C | 9948 | 28.6 | 214.2 | 7.3 |
| 4% S | 14359 | −3.1 | 202.8 | 1.7 |
| 4% I | 15882 | −14.0 | 209.2 | 4.8 |
| 2% C + 2% I | 7812 | 43.9 | 215.0 | 7.8 |
| 2% C + 2% S | 9562 | 31.4 | 220.0 | 10.3 |

From the table it can be seen that the combination of citric acid and the sugar gives benefits over and above the single active alone either in terms of volume or length. This demonstrates that the invention gives long lasting straightness benefits even after 1 wash.

The invention claimed is:

1. A method of straightening hair comprising:
   applying to the hair an aqueous hair treatment composition, consisting of:
   i) 0.4 to 2 wt % of the total hair treatment composition of sorbitol or isomalt,
   ii) 0.4 to 2 wt % of the total hair treatment composition of citric acid, and
   iii) 60 wt % or more of water, and
   after the applying the hair treatment composition, heating the hair to a temperature of greater than 120° C. for at least 10 seconds.

2. The method according to claim 1 in which the level of citric acid is 0.9 to 2 wt % of the hair treatment composition.

3. The method according to claim 1 in which the pH of the hair treatment composition is 4 or below at 20° C.

4. The method according to claim 1 in which the pH of the hair treatment composition is from 2.5 to 3.5 at 20° C.

5. The method according to claim 1 in which the hair is heated to the temperature above 150° C.

6. The method according to claim 1 in which the hair treatment composition is not washed off between the application of the hair treatment composition and the heating.

7. The method according to claim 6 in which the hair treatment composition is left on the hair for a minimum of 10 minutes before the heating.

* * * * *